US00PP28150P3

(12) United States Plant Patent
Adams

(10) Patent No.: US PP28,150 P3
(45) Date of Patent: Jul. 4, 2017

(54) APPLE TREE NAMED 'R10-45'

(50) Latin Name: *Malus domestica*
Varietal Denomination: R10-45

(71) Applicant: Kenneth Adams, Ephrata, WA (US)

(72) Inventor: Kenneth Adams, Ephrata, WA (US)

(73) Assignee: Regal Fruit International, LLC, Ephrata, WA (US)

( * ) Notice: Subject to any disclaimer, the term of this patent is extended or adjusted under 35 U.S.C. 154(b) by 63 days.

(21) Appl. No.: 14/545,401

(22) Filed: Apr. 30, 2015

(65) Prior Publication Data

US 2016/0324045 P1 Nov. 3, 2016

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Keith Robinson
(74) *Attorney, Agent, or Firm* — Randall Danskin P.S.

(57) ABSTRACT

A new and distinct variety of apple tree is described and which is characterized as to novelty by producing a flavorful apple which is mature for harvesting and shipment about October 4$^{th}$ under the ecological conditions prevailing in Quincy, Wash.

6 Drawing Sheets

Latin name: *Malus domestica.*
Varietal denomination: 'R10-45'.

BACKGROUND AND VARIETY

The present invention relates to a new, novel, and distinct variety of apple tree, and which has been denominated varietally as 'R10-45', and more specifically, to a novel apple tree which produces fruit which are ripe for harvesting and shipment at least about 2-4 weeks earlier than its male and female parents when grown under the same ecological conditions, and at the same geographical location.

ORIGIN AND ASEXUAL REPRODUCTION

It has long been recognized that an important factor contributing to the success of any new variety of apple tree bearing fresh market fruit is its relative date of harvesting as compared to other varieties bearing similar fruit in the same season. Additionally, another significant factor affecting the commercial viability of any new variety of apple relates to its appearance, as well as its storage characteristics, and which are reflected by such pomological traits as fruit pressure, soluble solids, and pH to name but a few. The new variety of apple tree, as described herein was derived by the following methodology. The new variety 'R10-45' was derived by way of a cross-pollination of the 'Honeycrisp' apple tree (the female parent, U.S. Plant Pat. No. 7,197) and a 'Cripps Pink' Cultivar (male parent, U.S. Plant Pat. No. 7,880), and wherein such cross pollination was made during the 2002 growing season. The resulting plant was then budded into 'M9' rootstock (unpatented), and the first fruit was observed in October 2007. After evaluation, and during the 2008 growing season, and in the month of April, second generation trees were budded onto 'M26' rootstock (unpatented), and which were then planted in the spring of 2009. The first fruit from these asexually reproduced trees were again observed in October 2010. Fruit generated from the second generation trees during the growing years 2010, 2011, 2012, 2013 and 2014 have been studied and compared and it appears that all characteristics of the subsequent asexually reproductive trees remain true to that seen in the original first generation tree.

SUMMARY OF THE NEW VARIETY

The 'R10-45' apple tree is characterized as to novelty by its date of maturity which is nearly two weeks earlier than its male parent, the 'Cripps Pink' Cultivar (U.S. Plant Pat. No. 7,880); and some four weeks following the harvesting of the female parent that being the 'Honeycrisp' apple tree (U.S. Plant Pat. No. 7,197) at the same geographical location. Additionally, the new variety of apple tree exhibits higher sugar levels than either of its parents, and has fruit pressures greater than what is seen in the fruit harvested from the 'Honeycrisp' apple tree (U.S. Plant Pat. No. 7,197), but which is less than the fruit pressure produced by the 'Cripps Pink' Cultivar (U.S. Plant Pat. No. 7,880). Additionally, it should be noted that the present variety produces fruit which have greater acid levels than the fruit produced by the 'Honeycrisp' apple tree, but which is further less than that of the 'Cripps Pink' Cultivar tree. The present variety of apple tree is similar to its parents inasmuch as the 'R10-45' has a long common storage life of at least 6 months. In contrast, however, the new variety of apple tree produces fruit which does not exhibit the bitter pit physiological disorder that the fruit produced by the 'Honeycrisp' apple tree (U.S. Plant Pat. No. 7,197) does on occasion.

BRIEF DESCRIPTION OF THE DRAWINGS

The accompanying drawings are color photographs of the present variety.

NOT A COMMERCIAL WARRANTY

Figure 1:
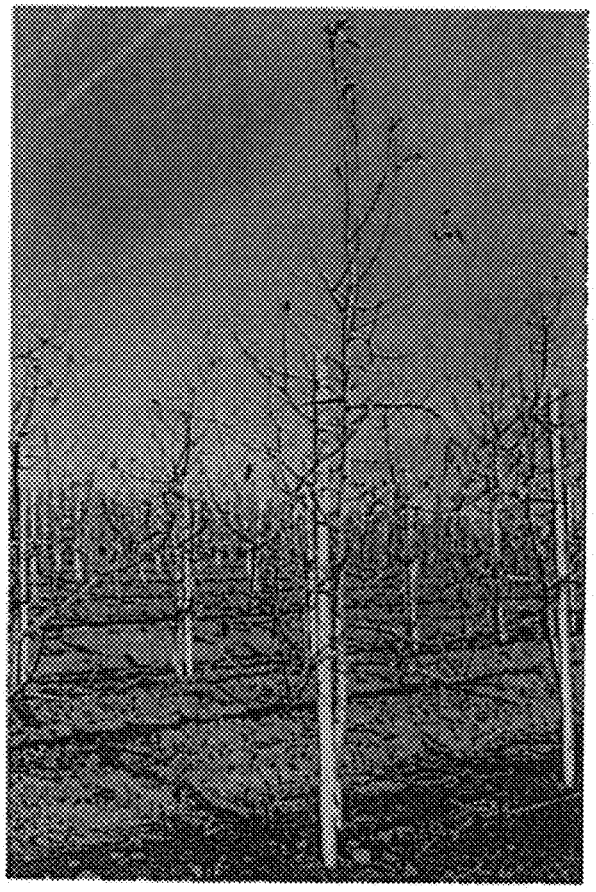
FIG. 1 depicts a second generation tree at full dormancy. This tree was established in 2008, and is a second generation tree.
Figure 2:
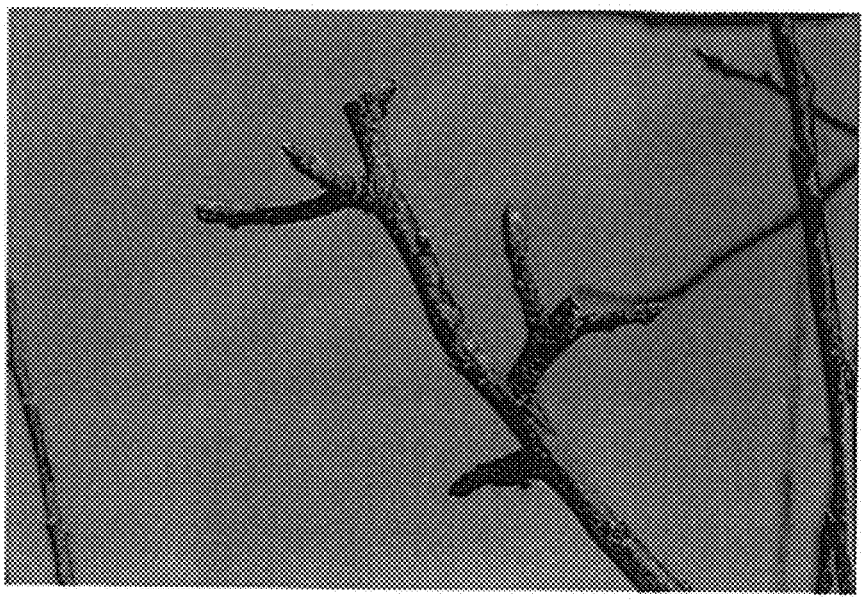
FIG. 2 shows the typical spur development shown by the new variety of apple tree. This tree was established in 2008, and is a second generation tree.
Figure 3:
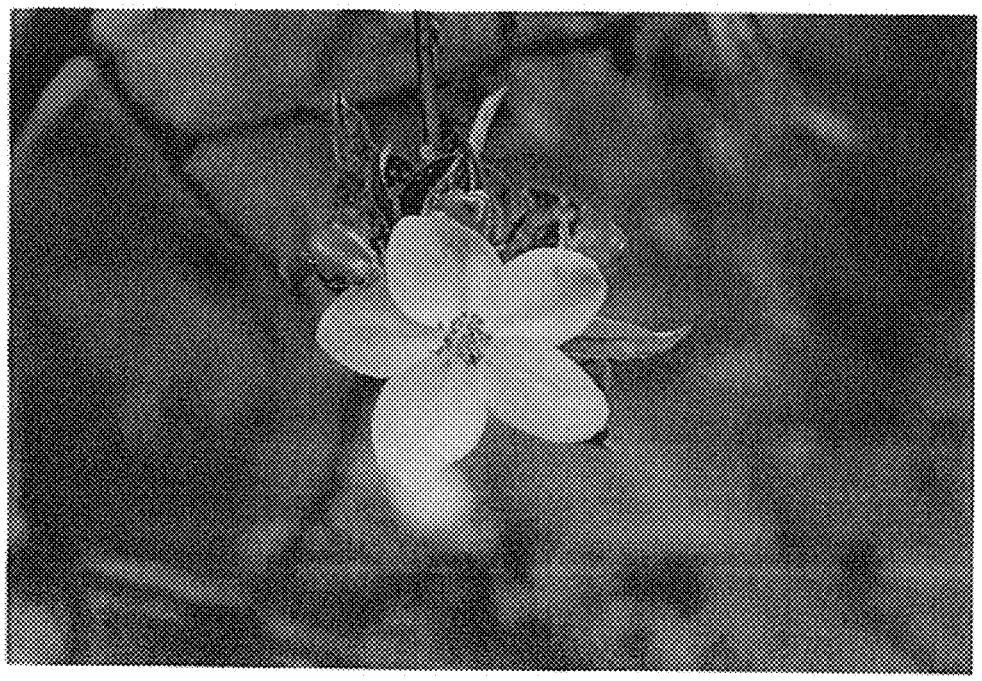
FIG. 3 illustrates the flowering characteristics of the new tree at full bloom and was taken from the tree as seen in FIG. 1.
Figure 4:
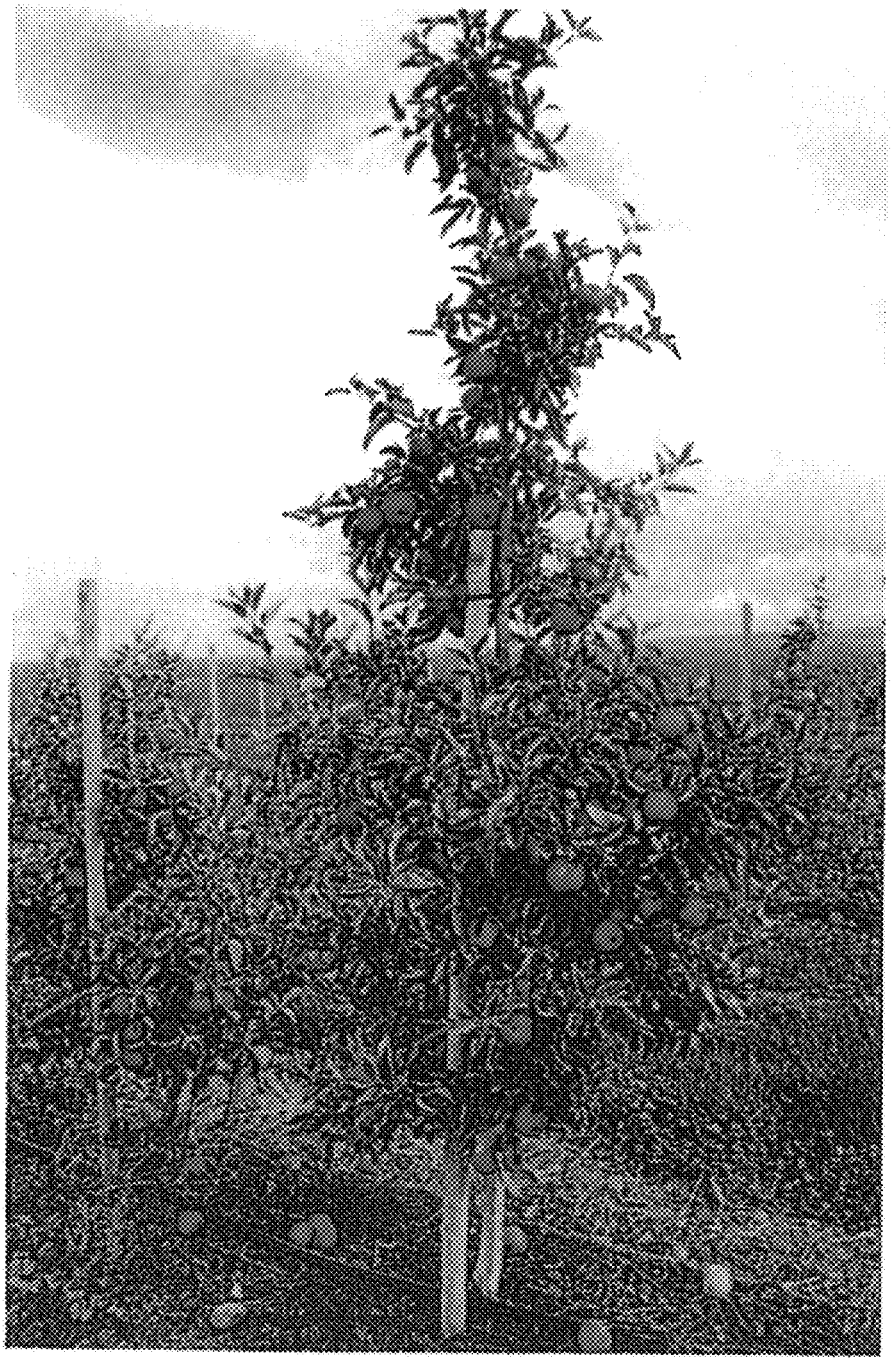
FIG. 4 shows the present tree at full harvest maturity. This photograph was taken of the first generation tree which is now 9 years old.
Figure 5:
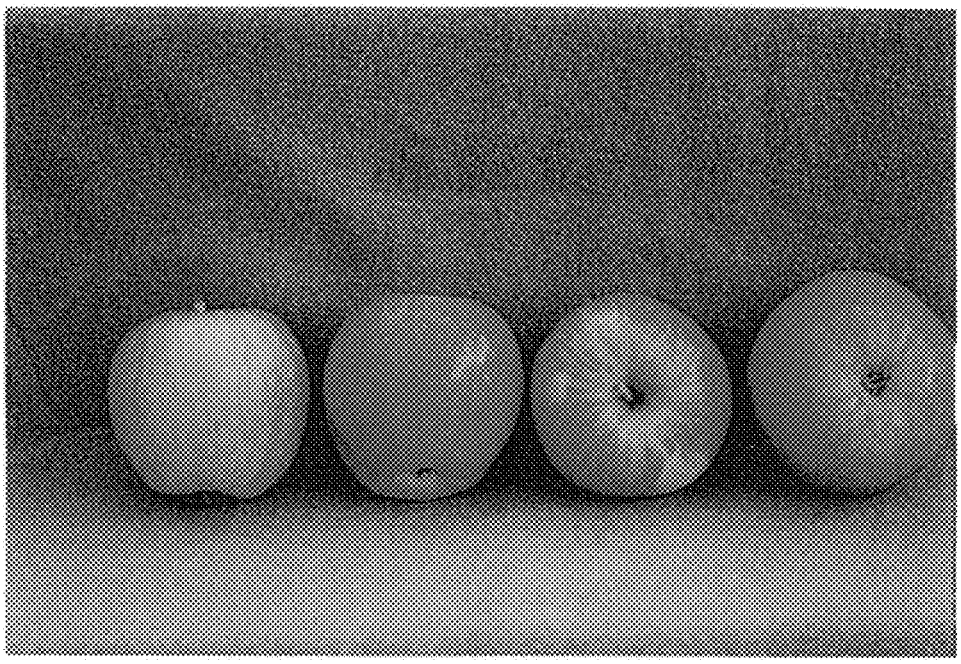
FIG. 5 shows the fruit produced by the present tree in various orientations. This fruit was harvested from a first generation tree which is now 9 years old.
Figure 6:
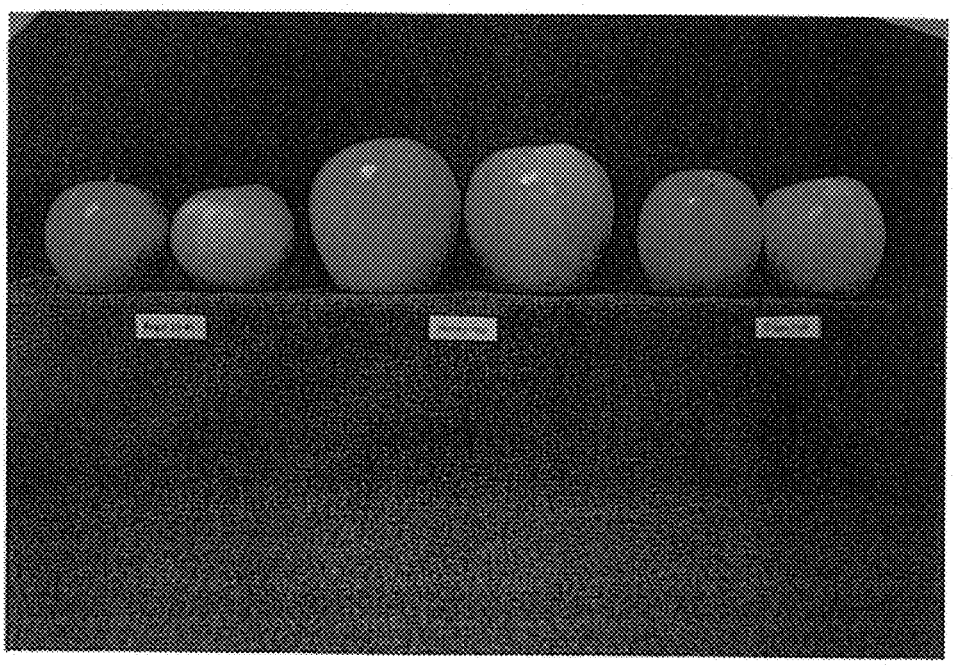
FIG. 6 illustrates the present variety of fruit as compared to the fruit produced by the 'Honeycrisp' apple tree (U.S. Plant Pat. No. 7,197), and that of the 'Cripps Pink' Cultivar (U.S. Plant Pat. No. 7,880). The fruit of the present variety was harvested from a tree that was 9 years old. The fruit harvested from the parent trees were both 20 years old.

The following detailed description has been prepared to solely comply with the provisions of 35 U.S.C. §112, and does not constitute a commercial warranty, (either expressed or implied), that the present variety will, in the future, display the botanical, pomological or other characteristics as set forth, hereinafter. Therefore, this disclosure may not be relied upon to support any future legal claims, including, but not limited to breach of warranty of merchantability, or fitness for any particular purpose, which is directed, in whole, or in part, to the present variety.

DETAILED DESCRIPTION

Referring more specifically to the pomological and botanical details of this new and distinct variety of apple tree which is now 9 years old, the following has been observed during the 2010 growing season under the ecological conditions prevailing in a test orchard which is located near Quincy, Wash. All major color code designations are by reference to The R.H.S. Colour Chart provided by The Royal Horticultural Society of Great Britain, 2001.

Tree:

*Tree type.*—The present variety is a spur-type tree with single buds appearing on each spur. The present tree is trained in a spindle-type manner.

*Fruit bearing.*—Considered a consistent bearer.

*Spur development.*—Generally — Moderate for the species.

*Tree vigor.*—Generally — Considered moderate.

*Tree shape.*—Generally — Upright and spreading as trained to the spindle.

*Tree height.*—The present variety, when measured during its ninth leaf, has an overall height of about 13 feet.

*Tree width.*—As measured during the ninth leaf, the new tree had a width of about 4.5 feet.

*Hardiness.*—Considered hardy for the current region where it is being grown in.

*Fruit productivity.*—Considered moderately heavy for the species. Under the growing conditions prevailing in 2010, on average, 57 pieces of fruit were harvested from each tree.

*Tree trunk.*—Size — The tree diameter is about 4.6 cm. when measured at a height of about 30 cm. above the graft union.

*Bark texture.*—Smooth.

*Bark color.*—Generally — Grey-orange (RHS N167A).

*Trunk lenticels.*—Generally speaking they are present, and moderate in number, and averaging about six lenticels in a four centimeter square area.

*Lenticel width.*—About 1.2 mm.

*Lenticel length.*—About 4.4 mm.

*Lenticel color.*—Generally — Brown, (RHS 200A).

*First year branches.*—Diameter — When measured at the midpoint of growth, the diameter is about 4.4 to about 6.9 mm.

*First year branch length.*—About 25.2 to about 64.5 cm.

*First year branch color.*—Grey-orange (RHS 166A).

*Branch lenticels.*—Numbers — Considered numerous and averaging about 20 per running cm. of growth.

*Lenticels.*—Shape — Round and having a diameter of about 0.8 to about 1.0 mm.

*Lenticel color.*—White (RHS 155D).

*Branch pubescence.*—Generally — Light to moderate pubescence covers about 100% of the surface area.

*Branch pubescence color.*—White (RHS 155D).

*Internodes.*—Generally — The distance between the nodes ranges from about 22.2 mm. to about 37.3 mm.

*Two year old fruiting branches.*—Generally — Two year old fruiting branches have a diameter when measured at the midpoint of growth of about 5.5 to about 6.8 mm.

*Two year old bark color.*—Grey-orange (RHS 165A).

*Two year old bark branch lenticels.*—Numbers — Numerous and averaging about 14 lenticels per square cm. of surface area.

*Lenticel shape.*—Generally elongated and a few being rounded.

*Lenticel length.*—About 1.2 to about 1.4 mm.

*Lenticel width.*—About 0.7 to about 0.8 mm. Lenticel Diameter — 0.9 to about 1.2 mm.

*Spur development.*—2 year old fruiting branches — Considered moderate.

*Spur length.*—About 11.8 to about 19.3 mm. The present variety is considered to be a tip bearer.

*Spur buds.*—Length — About 8.6 mm.

*Tip bud.*—Length — About 10.9 mm.

*Spur bud diameter.*—About 3.5 mm.

*Bud scale color.*—Grey-orange (RHS 178A).

*Scaffold branches.*—Size — About 19 mm. to about 20.4 mm. in diameter as measured at a distance of about 3 cm. from the trunk.

*Crotch angle.*—As presently spindle-trained it is about 90° when measured from the vertical.

*Branch color.*—Generally — Grey-orange (RHS N167A).

*Branch lenticel.*—Numbers — Numerous and averaging about 17 lenticels per 4 square centimeters of surface area.

*Lenticel shape.*—Elongated, about 0.4 to about 1 mm. in width and about 1.6 mm to about 3.7 mm. in length.

*Lenticel color.*—White (RHS N155D).

Leaves:

*Leaf shape.*—Generally — Narrowly acute.

*Dorsal surface texture.*—Glabrous, leathery, and undulating between the veins.

*Ventral surface texture.*—Considered smooth and having protruding veins.

*Surface sheen.*—A high sheen is seen on the dorsal surface.

*Leaf pubescence.*—This characteristic is only seen on the ventral surface. The leaf pubescence is fine, and moderate in density, and further extends over approximately 100% of the surface area.

*Leaf pubescence.*—Color — White (RHS 155C).

*Leaf length.*—Generally, the leaf length lies in a range of about 7.5 to about 11.2 cm.

*Leaf width.*—About 3.6 cm to about 6.2 cm.

*Marginal form.*—Generally — Considered serrate and occasionally bi-serrate.

*Leaf tip shape.*—Acuminate.

*Leaf base shape.*—Rounded. Leaf Base Attitude: Outward relative to the Shoot.

*Leaf color.*—Dorsal Surface — Yellow-green (RHS 147A).

*Leaf color.*—Ventral Surface — Yellow-green (RHS 147C).

*Mid-vein.*—Generally — Prominent and having considerable downiness over the entire undersurface.

*Mid-vein pubescence.*—Color — White (RHS 155C).

*Mid-vein width.*—When measured at mid-blade, this dimension averages 1.7 mm.

*Mid-vein color.*—Both the dorsal and ventral surface vein color is yellow-green (RHS 147C).

*Petiole.*—Length — About 21.5 to about 39.6 mm.

*Petiole surface texture.*—Generally — A shallow, and low groove extends along the entire length of the petiole.

*Petiole diameter.*—About 1.2 to about 2 mm.

*Petiole color.*—Dorsal surface — Yellow-green (RHS 147D).

*Petiole color.*—Ventral Surface — Yellow-green (RHS 145C).

*Petiole pubescence.*—Generally — Considered abundant, and having a moderate density over the entire length and circumference of the petiole.

*Petiole color.*—White. This color is not distinctive of the variety.

*Leaf stipules.*—Generally — Stipules are typically present. Usually two stipules are seen, and are present on about 50% of the leaves that are inspected.

*Stipule shape.*—Falcate.

*Stipule length.*—3.5 to about 10.3 mm.

*Stipule width.*—About 0.7 to about 1.4 mm.

*Stipule color.*—Dorsal Surface — Yellow-green (RHS 147A).

*Stipule color.*—Ventral Surface — Yellow-green (RHS 147C).

*Stipule pubescence.*—This characteristic is generally present on 100% of the ventral surface.

*Pubescence quantity.*—Light in quantity and having a white color (RHS 155C).

Flowers: Date of full bloom. In 2014 this was observed on April 24 under the ecological conditions prevailing in Quincy, Wash. Time of first bloom — In 2014 the first bloom was observed on April 19$^{th}$.

*Number of blossoms per bud.*—Generally — 5 to 6.

*Flower size.*—Generally — Considered large and having a diameter of about 42.3 to about 51.8 mm when fully opened.

*Petal numbers.*—5.

*Petal shape.*—Ovate. Petal Arrangement: Overlapping.

*Petal tip.*—Shape — Mostly rounded a few being obtuse or emarginated.

*Petal width.*—About 16.6 mm.

*Petal length.*—About 21.9 mm.

*Petal color.*—Unopened — Grey-purple (RHS 195B).

*Petal color when fully opened.*—The dorsal surface of the petal is a white color that graduates into a shade of grey-purple. (RHS 186D).

*Petal color.*—Ventral surface — White and having shades of grey-purple (RHS 186B).

*Stamens.*—Numbers — About 19 to 20.

*Filament.*—Length — About 5.6 to about 8.9 mm.

*Filament color.*—Grey-green (RHS 192C).

*Anthers.*—Shape — Kidney like.

*Anthers.*—Width — About 1.1 mm.

*Anthers.*—Length — About 1.9 mm.

*Anther color.*—Yellow-white (RHS 158B).

*Pollen production.*—Generally — Considered moderate in abundance.

*Pollen.*—Color — Yellow-white (RHS 158D).

*Pistil.*—Style — The style has a length of about 10.8 mm to about 13.7 mm.

*Style.*—Numbers — Five styles are fused at a distance of about 2.9 mm from the base.

*Style color.*—Grey-orange (RHS 163D).

*Style.*—Pubescence — This pubescence is typically found in a region from the base to the fused region.

*Pubescence color.*—Green-white (RHS 155C).

*Stigma.*—Shape — Club like.

*Stigma color.*—Grey-yellow (RHS 162A).

*Stigma.*—Pollen Abundance — Considered abundant.

*Mature pollen color.*—Yellow-white (RHS 158D).

*Sepals.*—Numbers — 5 per blossom.

*Sepals.*—Shape — Lanceolate and the sepal tip being acuminate in shape.

*Sepal base.*—Shape — Truncate.

*Sepal length.*—About 9.1 mm. Sepal Width — About 4.3 mm.

*Sepals.*—Pubescence — Abundant, and further covers both of the dorsal and ventral surfaces.

*Pubescence color.*—White (RHS 155C).

*Sepal color.*—Dorsal and Ventral Surfaces — Yellow-green (RHS 146C).

*Sepal color.*—Tips — Highlighted, and appear grey-purple (RHS 182A).

*Peduncle.*—Length — About 13.8 to about 25.9 mm.

*Peduncle.*—Diameter — About 1.1 mm to about 1.5 mm.

*Peduncle color.*—The shaded side of the peduncle has a yellow-green color (RHS 146A). The exposed side of the peduncle is grey-green (RHS 197A).

*Downiness.*—Generally — A moderately heavy white downiness is present over the entire surface.

*Downiness color.*—White (RHS 155C).

*Thalamus depth.*—About 2.3 to about 3.1 mm.

Fruit:

*Generally.*—The observations which follow have been taken from the first generation tree fruit.

*Fruit form.*—Considered flat-round.

*Equatorial diameter.*—Generally irregular, and occasional ribbing is observed. The current variety is lopsided in appearance and typically 5 crowns appear which are slightly pronounced.

*Fruit size.*—Generally — Small to medium at normal crop levels.

*Equatorial diameter.*—About 7.7 cm.

*Axial diameter (fruit height).*—6.4 cm.

*Fruit stem.*—Generally — Generally considered medium in length, about 15 mm. to about 30.5 mm.

*Fruit stem.*—Width — The diameter of the fruit stem, when measured at mid-length, ranges from about 1.9 mm. to about 3.8 mm.

*Stem cavity.*—Width — The width ranges from about 28 to about 33.7 mm.

*Stem cavity.*—Depth — About 14.3 mm.

*Stem cavity shape.*—Obtuse and russetted. No lipping is observed.

*Basin cavity.*—Shape — The basin cavity is lightly ribbed and the sides are considered sloping.

*Basin cavity.*—Width — About 28.5 to 33.7 mm.

*Basin cavity.*—Depth — About 6.2 to about 10.9 mm.

*Basin cavity surface texture.*—Downy at the base. The pubescence is white (RHS 155A).

*Eye.*—Generally — Considered erect and having an occasional, reflexed tip. Eye Basin Russet: Absent to only a very little is present.

*Eye.*—Surface Texture — Generally a light downiness is observed at the base. This downiness has a white color (RHS 155A). Eye Width: About 25.7 to about 31.3 mm.

*Sepal color.*—Yellow-green (RHS 148B).

*Fruit skin.*—Generally — The appearance of the skin is blotched in appearance over 95% to about 100% of the fruit surface. Faint stripping appears over less than about 5% of the fruit surface. Stripping width: About 1 mm. to about 5 mm.

*Fruit skin color.*—This appears as a blotched over-color which is red (RHS 46A). The under-color is washed and appears grey-yellow (RHS 160). Bloom — Generally considered light.

*Stripe color.*—Red (RHS 53A).

*Fruit skin thickness.*—Considered thin, about 0.2 mm.

*Skin texture.*—Brittle, and tender.

*Fruit skin lenticels.*—Present, prominent and evenly distributed.

*Lenticel numbers.*—Generally 4 per square cm. of fruit skin surface area.

*Lenticel shape.*—Round and having a diameter of about 0.4 to 0.6 mm.

*Lenticel color.*—White (RHS 155D).

*Core.*—Position — Sessile.

*Core line position.*—Clasping.

*Core shape.*—Flat; round.

*Core length.*—About 24.6 to about 28.3 mm.

*Core diameter.*—About 32.5 to about 41.7 mm.

*Cell.*—Generally — Not tufted.

*Cell shape.*—Cordate.

*Cell length.*—About 15.4 mm.

*Cell width.*—About 10.6 mm. Cell Depth: When measured wall-to-wall it is about 5.6 mm.

*Tube.*—Shape — Funnel.

*Stamen position.*—Generally considered median.

*Axis.*—Generally — Axile and open.

*Seeds.*—Numbers — 1-2.

*Seed shape.*—Obtuse.

*Seed length.*—About 7.4 mm.

*Seed width.*—When measured suture-to-suture it is about 4.5 mm.

*Seed width.*—When measured wall-to-wall — This is about 2.9 mm.

*Seed color.*—Grey-orange (RHS 176C).

*Flesh.*—Generally — Considered crisp, melting and juicy.

*Flesh flavor.*—Considered subacid, and apple-like.

*Flesh browning.*—This characteristic is observed typically 10-15 minutes following the cutting of the apple.

*Flesh color.*—White (RHS 158D).

*Flesh aroma.*—Mild, and apple like.

*Date of maturity for harvesting and shipment.*—About Oct. 4, 2014 under the ecological conditions prevailing in Quincy, Wash. This is in contrast to the harvest date of the 'Honeycrisp' Apple trees (U.S. Plant Pat. No. 7,197) and which were harvested on Sep. 9, 2014, and the 'Cripps Pink Cultivar' trees (U.S. Plant Pat. No. 7,880), and which were harvested on Oct. 15, 2014 at Quincy, Wash.

*Starch.*—Generally — At harvest maturity the apples have a starch of about 3.0.

*Fruit pressure.*—At harvest maturity the present variety has a fruit pressure of about 17.1 lbs. This is in contrast to the fruit produced by the 'Honeycrisp' apple tree which has a fruit pressure of about 15 lbs and the fruit produced by the 'Cripps Pink' Cultivar apple tree which has a fruit pressure of about 19.4 lbs.

*Brix.*—At harvest maturity the present variety has a brix of about 14.7. This is in contrast to the fruit produced by the 'Honeycrisp' apple tree at the same geographical location, and which has a brix of about 13.5 and that of the 'Cripps Pink' Cultivar apple tree, and which has a brix of about 14.

*Acid content.*—When measured at harvest maturity the present variety has an acid contents of about 5.88 grams per liter. This is in contrast to the fruit produced by the Honeycrisp apple tree, and which has an acid content of about 5.11, and that of the Cripps Pink Cultivar apple tree, and which has an acid content of about 6.64 at full harvest maturity.

*ph.*—At harvest maturity the present variety has a pH of 3.45. This is in contrast to the fruit produced by the 'Honeycrisp' and 'Cripps Pink' Cultivar trees which produce fruit at harvest maturity having a pH of about 3.45 and 3.27, respectively.

*Keeping quality.*—Considered very good. Fruit has been kept up to 6 months in common storage with no deleterious effects noted.

*Pollination.*—Generally — Any diploid apple having the same blooming season may be utilized.

*Fruit use.*—A dessert apple. The present variety has excellent eating quality and has a snappy, juicy, sweet and melting skin.

*Disease and insect resistance.*—The present variety is anticipated to be susceptible to the known insects and known diseases found in the region of Central Washington State. Fruit as observed does not exhibit any physiological disorders on the tree nor during storage for the duration of normal lengths. The following chart identifies the known insects and known diseases, including the common and Latin names thereof, that are found in the region of Central Washington State. The listing is provided in order to supply a complete disclosure for patent purposes.

Known Insects

| Common Name | Latin Name | Genus | Species |
|---|---|---|---|
| Apple Aphid | *Aphis pomi* | *Aphis* | *A. pomi* |
| Apple Ermine Moth | *Yponomeuta malinella* | *Yponomeuta* | *Y. malinella* |
| Apple Magot | *Rhagoletis pomonella* | *Rhagofetis* | *R. pomonella* |
| Apple Rust Mite | *Aculus schlectendali* | *Aculus* | *A. schlectendali* |
| Brown Marmorated Stink Bug | *Haiyomorpha halys* | *Halyomorpha* | *H. halys* |
| Codling Moth | *Cydia (Laspeyresia) pomonella* | *Cydia* | *C. pomonelia* |
| Leafroller | *Archips roanus* | *Archips* | *A. roanus* |
| Rosy Apple Aphid | *Dysaphis plantaginea* | *Dysaphis* | *D. plantaginea* |
| San Jose Scale | *Quadraspidiotus perniciosus* | *Quadraspidiotus* | *Q. perniciosus* |
| Woolly Apple Aphid | *Eriosoma lanigerum* | Eriosoma | *E. lanigerum* |

| Common name | Scientific name | Order: Family |
|---|---|---|
| Ambrosia beetle (European shothole borer) | *Xyleborus dispar* Fabricius | Coleoptera:Scolytidae |
| Apple aphid | *Aphis pomi* De Geer | Homoptera: Aphididae |
| Apple ermine moth | *Yponomeuta malinellus* (Linnaeus) | Lepidoptera: Yponomeutidae |
| Apple grain aphid | *Rhopalosiphum fitchii* (Sanderson) | Homoptera: Aphididae |
| Apple maggot | *Rhagoletis pomonella* (Walsh) | Diptera: Tephritidae |
| Apple rust mite | *Aculus schiechtendali* (Nalepa) | Acari: Eriophyidae |
| Appleleaf blister mite | *Phytoptus mali* (Burts) | Acari: Eriophyidae |
| Bertha armyworm | *Mamestra configurata* Walker | Lepidoptera: Noctuidae |
| Black cherry aphid | *Myzus cerasi* (Fabricus) | Homoptera: Aphididae |
| California pear sawfly | *Pristophora abbreviata* (Hartig) | Hymenoptera: Tenthredinidae |
| Campylomma | *Campylomma verbasci* (Meyer) | Hemiptera: Miridae |
| Cherry bark tortrix | *Enarmonia formosana* (Scopoli) | Lepidoptera: Tortricidae |
| Cherry fruit fly | *Rhagoletis indifferens* Curran | Diptera: Tephritidae |
| Clearwinged grasshopper | *Camnula pellucida* (Scudder) | Orthoptera: Locustidae |
| Codling moth | *Cydia pomonella* (Linnaeus) | Lepidoptera: Tortricidae |
| Consperse stink bug | *Euschistus conspersus* Uhler | Hemiptera: Pentatomidae |
| Dock sawfly | *Ametestegia glabrata* (Fallén) | Hymenoptera: Tenthredinidae |
| European leafroller | *Archips rosanus* (Linnaeus) | Lepidoptera: Tortricidae |
| European earwig | *Forficula auricularia* (Linnaeus) | Dermaptera: Forficulidae |
| European fruit lecanium | *Parthenolecanium corni* (Bouché) | Homoptera: Coccidae |

-continued

| | | |
|---|---|---|
| European red mite | *Panonychus ulmi* (Koch) | Acari: Tetranychidae |
| Eyespotted bud moth | *Spilonota ocellana* (Denis & (Schiffermüller) | Lepidoptera: Tortricidae |
| Fall webworm | *Hyphantria cunea* Drury | Lepidoptera: Arctiidae |
| Forest tent caterpillar | *Malacosoma disstria* Hébner | Lepidoptera: Lasiocampidae |
| Fruittree leafroller | *Archips argyrospilus* (Walker) | Lepidoptera: Tortricidae |
| Grape mealybug | *Pseudococcus maritimus* (Ehrhorn ) | Homoptera: Coccidae |
| Green fruitworm | *Lithophane antennata* (Walker) | Lepidoptera: Noctuidae |
| Green peach aphid | *Myzus persicae* (Sulzer) | Homoptera: Aphididae |
| Green stink bug (green soldier bug) | *Acrostemum hilare* (Say) | Hempitera: Pentatomidae |
| Hop aphid | *Phorodon humuli* (Schrank) | Homoptera: Aphididae |
| Leafcurl plum aphid | *Anuraphis helichrysi* (Kallenbach) | Homoptera: Aphididae |
| Lesser appleworm | *Grapholitha prunivora* (Walsh) | Lepidoptera: Tortricidae |
| Lesser shothole borer (Ambrosia beetle) | *Xyleborus saxeseni* Ratzeburg | Coleoptera: Scolytidae |
| Lygus bug (Tarnished plant bug) | *Lygus lineolaris* (Palisot de Beauvois) | Hemiptera: Miridae |
| McDaniel spider mite | *Tetranychus mcdanieli* McGregor | Acari: Tetranychidae |
| Mealy plum aphid | *Hyalopterus pruni* (Geoffroy) | Homoptera: Aphididae |
| Migratory grasshopper | *Melanopus sanguinipes* (Fabricius) | Orthoptera: Locustidae |
| Obliquebanded leafroiler | *Choristoneura rosaceana* (Harris) | Lepidoptera: Tortricidae |
| Oriental fruit moth | *Grapholitha molesta* (Busck) | Lepidoptera: Tortricidae |
| Oystershell scale | *Lepidosaphes ulmi* (Linnaeus) | Homoptera: Diaspididae |
| Pacific flatheaded borer | *Chrysobothris mali* Horn | Coleoptera: Buprestidae |
| Pandemis leafroller | *Pandemis pyrusana* Kearfott | Lepidoptera: Tortricidae |
| Peach silver mite | *Aculus fockeui* (Nalepa & Trouessart) | Acari: Eriophyidae |
| Peach twig borer | *Anarsia lineatella* Zeller | Lepidoptera: Gelechildae |
| Peachtree borer | *Synanthedon exitiosa* (Say) | Lepidoptera: Sesiidae |
| Pear leafcurling midge | *Dasyneura pyri* Bouché | Diptera: Cecidomyiidae |
| Pear psylla | *Cacopsylla pyricola* (Foerster) | Homoptera: Psyllidae |
| Pear rust mite | *Epitrimerus pyri* (Nalepa) | Acari Eriophyidae |
| Pear sawfly (pear slug) | *Caliroa cerasi* (Linnaeus) | Hymenoptera: Tenthredinidae |
| Pearleaf blister mite | *Phytoptus pyri* Pagenstecher | Acari: Eriophyidae |
| Prunus rust mite | *Aculus fockeui* (Nalepa & Trouessart) | Acari: Eriophyidae |
| Pyramidal fruitworrn | *Amphipyra pyramidoides* (Guenée) | Lepidoptera: Noctuidae |
| Rain beetles | *Pleocoma* spp. | Coleoptera: Scarabaeidae |
| Redhumped caterpillar | *Schizura concinna* (J. E. Smith) | Lepidoptera: Notodontidae |
| Redlegged grasshopper | *Melanoplus femur-rubrum* (De Greer) | Orthoptera: Locustidae |
| Rose leafhopper | *Edwardsiana rosae* (Linneaus) | Homptera: Cicadellidae |
| Rosy apple aphid | *Dysaphis plantaginae* Passerini | Homptera: Aphididae |
| Rusty plum aphid | *Hysteroneura setariae* (Thomas) | Homoptera: Aphididae |
| San Jose scale | *Quadraspidiotus perniciosus* (Comstock) | Homoptera: Diaspididae |

-continued

| | | |
|---|---|---|
| Shothole borer | *Scolytus rugulosus* | Coleoptera: Scolytidae |
| Speckled green fruitworm | *Orthosia hibisci* | Lepidoptera: Noctuidae |
| Spirea aphid | *Aphis spiraecola* Patch | Homptera: Aphididae |
| Spotted cutworm | *Xestia* (*Amathes*) *c-nigrum* (Linnaeus) | Lepidoptera: Noctuidae |
| Spotted wing drosophila | *Drosophila suzukii* (Matsumura) | Diptera: Drosophilidae |
| Tenlined June beetle | *Polyphylla decemlineata* (Say) | Coleoptera: Scarabaeidae |
| Thistle aphid | *Brachycaudus cardui* (Linnaeus) | Homoptera: Aphididae |
| Twospotted spider mite | *Tetranychus urticae* Koch | Acari: Tetranychidae |
| Variegated cutworm | *Peridroma saucia* (Hübner) | Lepidoptera: Noctuidae |
| Walnut husk fly | *Rhagoletis completa* Cresson | Diptera: Tephritidae |
| Western boxelder bug | *Leptocoris rubrolineatus* Barber | Hempitera: Rhopalidae |
| Western flower thrips | *Frankliniella occidentalis* (Pergande) | Thysanoptera: Thripidae |
| Western tent caterpillar | *Malacosomo fragilis* (Stretch) | Lepidoptera: Lasiocampidae |
| Western tentiform leafminer | *Phyllopnorycter elmaella* Doganlar & Mutuura | Lepidoptera: Gracillarlidae |
| White apple leafhopper | *Typhlocyba pomaria* McAtee | Homoptera: Cicadellidae |
| Woolly apple aphid | *Eriosoma lanigerum* (Hausman) | Homoptera: Aphididae |
| Yellonecked caterpillar | *Datana ministra* Drury | Lepidoptera: Notodontidae |
| Yellow spider mite | *Eotetranychus carpini borealis* (Ewing) | Acari: Tetranychidae |

Known Diseases

| Common Name | Latin Name (Causal Agent) | Genus | Species |
|---|---|---|---|
| Apple Scab | *Venturia inaequalis* | *Venturia* | *V. inaequalis* |
| Fire Blight | *Erwinia amylovora* | *Erwinia* | *E. amylovora* |
| Powdery Mildew | *Podosphaera leucotricha* | *Podosphaera* | *P. leucotriche* |

Although the new variety of apple tree possesses the described characteristics when grown under the ecological conditions prevailing in Quincy, Wash., in the south central part of Washington state, it should be understood that variations of the usual magnitude and characteristics incident to changes in growing conditions, fertilization, pruning and pest control as well as horticultural management practices are to be expected.

Having thus described and illustrated my new variety of apple tree, what I claim is new and desire to secure by plant Letters Patent is:

1. A new and distinct variety of apple tree, substantially as illustrated and described, and which is characterized principally as to novelty by bearing a flavorful apple which is mature for harvesting and shipment about October $4^{th}$ under the ecological conditions prevailing in Quincy, Wash.

* * * * *